(12) United States Patent
Jonasson Bjäräng

(10) Patent No.: US 7,830,530 B2
(45) Date of Patent: Nov. 9, 2010

(54) DEVICE AND METHOD FOR OPTICAL MEASUREMENT OF GRAINS FROM CEREALS AND LIKE CROPS

(75) Inventor: Tomas Jonasson Bjäräng, Munka Ljungby (SE)

(73) Assignee: Foss Analytical AB., Höganäs (SE)

( * ) Notice: Subject to any disclaimer, the term of this patent is extended or adjusted under 35 U.S.C. 154(b) by 0 days.

(21) Appl. No.: 12/224,091

(22) PCT Filed: Jan. 30, 2007

(86) PCT No.: PCT/EP2007/050901

§ 371 (c)(1),
(2), (4) Date: Aug. 18, 2008

(87) PCT Pub. No.: WO2007/099008

PCT Pub. Date: Sep. 7, 2007

(65) Prior Publication Data

US 2009/0021751 A1    Jan. 22, 2009

(30) Foreign Application Priority Data

Mar. 2, 2006    (EP) .................................. 06110604

(51) Int. Cl.
*G01B 11/24* (2006.01)
(52) U.S. Cl. .................. 356/601; 250/225; 250/339.06; 250/341.8; 356/625; 356/637
(58) Field of Classification Search .................. 250/225, 250/339.01, 339.06, 341.8; 356/601, 625, 356/628, 637
See application file for complete search history.

(56) References Cited

U.S. PATENT DOCUMENTS

| | | | | |
|---|---|---|---|---|
| 5,480,354 A | * | 1/1996 | Sadjadi ........................ | 460/149 |
| 5,917,927 A | | 6/1999 | Satake et al. | |
| 5,956,413 A | * | 9/1999 | Oste et al. .................... | 382/110 |
| 5,957,773 A | * | 9/1999 | Olmsted et al. ............. | 460/149 |
| 6,369,401 B1 | * | 4/2002 | Lee ............................. | 356/627 |
| 2005/0074146 A1 | | 4/2005 | Jones et al. | |
| 2005/0231734 A1 | | 10/2005 | Johannesson et al. | |
| 2007/0224530 A1 | * | 9/2007 | Kobori et al. ............... | 430/100 |

FOREIGN PATENT DOCUMENTS

| | | |
|---|---|---|
| JP | 2005 133905 | 5/1993 |
| JP | 2003 139443 | 5/2002 |
| JP | 2002 310919 | 10/2002 |

* cited by examiner

*Primary Examiner*—Gregory J Toatley, Jr.
*Assistant Examiner*—Iyabo S Alli
(74) *Attorney, Agent, or Firm*—Harness, Dickey & Pierce, P.L.C.

(57) ABSTRACT

A device for optical measuring of grains for analysis of the quality of the grains, comprises a feeder which is arranged to feed at least one grain in a direction of transport, a light source which is arranged to illuminate the grain along a line, a detector which is arranged to detect reflection from the surfaces of the grain and an analyzer which is arranged to analyze the detected reflection in order to determine a height profile of the grain along the line and to determine three-dimensional surface topographical information on the grain based on a plurality of determined height profiles as the grain is transported. The device further comprises an arrangement used in generating a two-dimensional image and the analyzer is arranged to determine a quality of the grain based on the three-dimensional surface information and the two-dimensional image of the same grain.

8 Claims, 11 Drawing Sheets

DEVICE AND METHOD FOR OPTICAL MEASUREMENT OF GRAINS FROM CEREALS AND LIKE CROPS

This invention relates to a device and a method for optical measuring of individual grains from cereals and like crops, for analysis of the quality of the crop.

Inspection of different kinds of cereals and other crops is today made all over the world to determine the quality of the cereals in commercial transactions and handling. The inspection aims at examining a selected representative sample from a large consignment and determining the presence of non-desirable grains and particles. The non-approved grains and particles are classified and the quantity of each class is determined. Owing to the distribution of the various grains, the sample and, thus, the consignment will be given a grading which is a decisive factor in connection with payment and handling of the consignment.

Today most cereal inspections are carried out in automated processes. Presently, use is often made of certain optical measuring methods for determination of the quality of the grains by monitoring external, surface properties of the grain. Such a measuring method is typically based on a grain being illuminated, whereupon a two-dimensional (2D) image of the individual grain is obtained for analysis in order to determine the quality of the grain consignment. The analysis may e.g. comprise determining the colour of the grain and/or size and shape of the grain. Each grain may then be classified and may be segregated into different qualities. One such method for grading and classifying grain is described in US2005/0074146.

A device for three-dimensional (3D) optical volume measurements of oysters and agricultural materials, such as corn, is disclosed in U.S. Pat. No. 6,369,401. The device comprises a laser and detector mutually arranged to generate displacement data resulting from the laser emission impinging a surface of an object under inspection. An analyzer processes this data to generate height information which is used together with boundary information derived from a binary 2D image to calculate a volume of the object under inspection. This provides for grading and classifying grain based solely on volume.

Thus, using known methods and devices non-approved grains and other particles may be sorted out. Further, a measure of the relative occurrence of non-approved grains and undesired particles may be used for setting the price of the consignment. Traditionally, weight has been a factor for comparison between approved and non-approved grains and particles, that is, the different qualities are sorted out and weighed. Alternatively, the relative total volumes of the approved and non-approved grains and particles may be used for setting the price of the consignment.

It is desired to enable improved identification of different grades of grains and also to provide accurate measures of the relative volumes of different grades.

It is a particular objective of the present invention to provide for a consistent, rapid and accurate analysis of grain for various visual quality factors, especially a surface based quality factor. It is furthermore an object of the present invention to reduce the subjectivity inherent in conventional visual grain quality assessment, and consequently, to aid in making better decisions in the processes of grain analysis.

Another objective of the present invention is to provide improved accuracy in the identification of visually discernable defects in a grain sample, particularly the identification of defects in grains related to the geometrical aspects such as the surface structure (or topography).

The above objects, advantages and features together with numerous other objects, advantages and features, which will become evident from the below detailed description, are obtained according to a first aspect of the present invention by a device for optical measuring of grain from crops, for analysis of the quality of the crop as defined in and characterised by the present Claim 1 and according to second aspect of the present invention by a method as defined in and characterised by the present Claim 7.

By means of an advantageous embodiment of the invention, there is provided a device which enables 2D images and 3D surface information (topographical information) of individual grains to be obtained for a same one or more individual grains. Further, the device uses the 3D information in combination with the 2D image in order to assess quality of the crop, the grains from which constitute the sample under analysis. The 3D information is particularly suited for, for example, detecting defects, such as irregular shapes or cracks, in particles, and determining the volume of the grain, which may be used for classifying individual grains or determining a volume percentage of different grades of grain in the grain sample.

By analyzing the spatially collocated 3D and 2D information for the same grain then determining the quality of the crop and/or individual grain can be done by the device in a quick and direct manner.

By means of this embodiment, the device enables accurate determination of 3D surface information of at least one grain. The 3D surface information may be mapped on to the 2D image of the same grain and in combination used for determining features to be employed in assessing the quality of grains and/or crops from which the grain sample was taken. These so determined features of the individual grain may be used solely or in combination with features from other measuring methods in order to determine the desired quality.

In other words, by using a detector in combination with a light source to measure how the height of individual grains in a sample varies, detailed surface structure information is obtained. This information, in combination with the 2D image information can also be used for a more accurate classification and/or detection of defects of grain. Hence, the device discloses a tool to more effectively and precisely assess quality of agricultural commodities.

According to one embodiment, the analyzer is adapted to determine a quality that also is dependant on a volume measurement for at least one grain of the crop sample. By means of the determined heights, a very accurate volume of each grain may be calculated. An individual grain may be assigned to a specific quality based also on its volume. Additionally or alternatively, the grain sample or an entire consignment of grain may be assigned to a specific quality wherein the volume of, for example, approved grains are related to the volume of non-approved grains.

The analyzer may be adapted to determine a quality that comprises classification and/or identification of a defect in the individual grain and/or the sample. The determined 3D surface information may be used to identify abnormal or undesirable shapes of the grain and this, alone or together with the 2D image information, then employed to identify defects related to such undesired shapes. Also, the determined 3D surface information may be used to classify an individual grain as belonging to a specific grade.

The defect under consideration may be a cracked, split, or irregularly shaped grain, weather damage, skin remainders, sprouted kernels, mould and/or fungal diseases, rougher surface or any combinations thereof.

The detector may comprise an image-acquiring means which is arranged at a non-perpendicular angle to a plane, such as may be provided by a surface of a conveyor belt, on which the sample is fed. This allows the image-acquiring means to view different heights in relation to the plane in different rows of the image. Further, the analyzer may be adapted to determine the height profile by comparing distances from the surface of the grain with the distance from the plane.

However, the optical measurement can be any kind of light-sensitive measurement. The detector need not record an image, but can record the light intensity in certain points or some kind of averaging among a plurality of properties, such as directly reflected light compared with diffusely reflected light. The image-acquiring means could be, for instance, any type of digital camera, such as a CMOS camera.

The light source for 3D measurements may comprise a laser light source. Hereby, a significant contrast difference between the illuminated section and the remainder of the sample is achieved. Thus, precise height measurements of the sample are enabled with high resolution. Usefully, the laser light source is arranged to emit light in a plane, preferably perpendicular to both the plane on which the grain sample is fed and to the direction of movement of the grain sample on that plane. Thus, the height profile may be simultaneously determined over a cross-section of an individual grain sample and thus for a large number of grains being arranged side by side.

The cooperating detector may comprise two or more units, which are arranged to detect reflected light from at least partially different regions of the individual grains. This is especially advantageous when the detector is arranged at a non-perpendicular angle to the plane on which the grain sample is fed. In such case, parts of a particle may be obscured to a detector and having two or more units would aid in obtaining information of the height profile from all parts of the grain samples.

The feeder may comprise a conveyor. The feeder need not transport the grain sample during continuous movement in an essentially straight line but in most cases it is advantageous since a conventional conveyor belt can be used for this purpose. The feeder may also or alternatively comprise an inclined surface such that the sample is fed to the place for optical measurement under the influence of gravity.

According to an embodiment, the detector for obtaining a 2D image is relatively disposed to obtain a 2D plan view of the grain sample. Usefully, the analyzer is adapted to process the 2D plan view and the collocated three-dimensional image information to determine a quality of said particle sample. The use of a 2D plan view makes the collocation with the 3D height information computationally simpler, thus speeding up the analysis by the device. Additionally or alternatively the 2D image may be employed in the analyzer to differentiate foreign objects from grains within the grain sample. This information may itself be used in the analyser in the determination of a quality of the crop or may be used to limit the further analysis using the 3D information to objects identified as being grains. Conversely, the 3D height information may be used to differentiate between grains and foreign objects in the sample under analysis. Typically, foreign objects such as stones or stalks may produce plan view images of similar dimensions to those of grains. However such objects tend to differ largely in height from the heights of grains The device may be arranged to determine a quality to be used as a basis for pricing of crops. The pricing of crops may typically be determined by the relative volume of approved grains or specific grades in the sample.

The device may also or alternatively be arranged to select grains of similar outer dimensions and visual characteristics. These outer dimensions and visual characteristics may then be used in the device for sorting grains of similar outer properties, which may be useful for later handling of the grains.

The above objects, advantages and features as well as additional objects, advantages and features of the present invention will be better understood through the following illustrative and non-limiting detailed description of exemplary embodiments of the present invention, done with reference to the drawings in the appended Figures, wherein.

In the following description reference is made to the accompanying figures which form a part hereof and in which is shown by way of illustration an embodiment of how the invention may be practiced. It is to be understood that other embodiments may be utilized and structural and functional modifications may be made without departing from the scope of the present invention.

Figure 1:
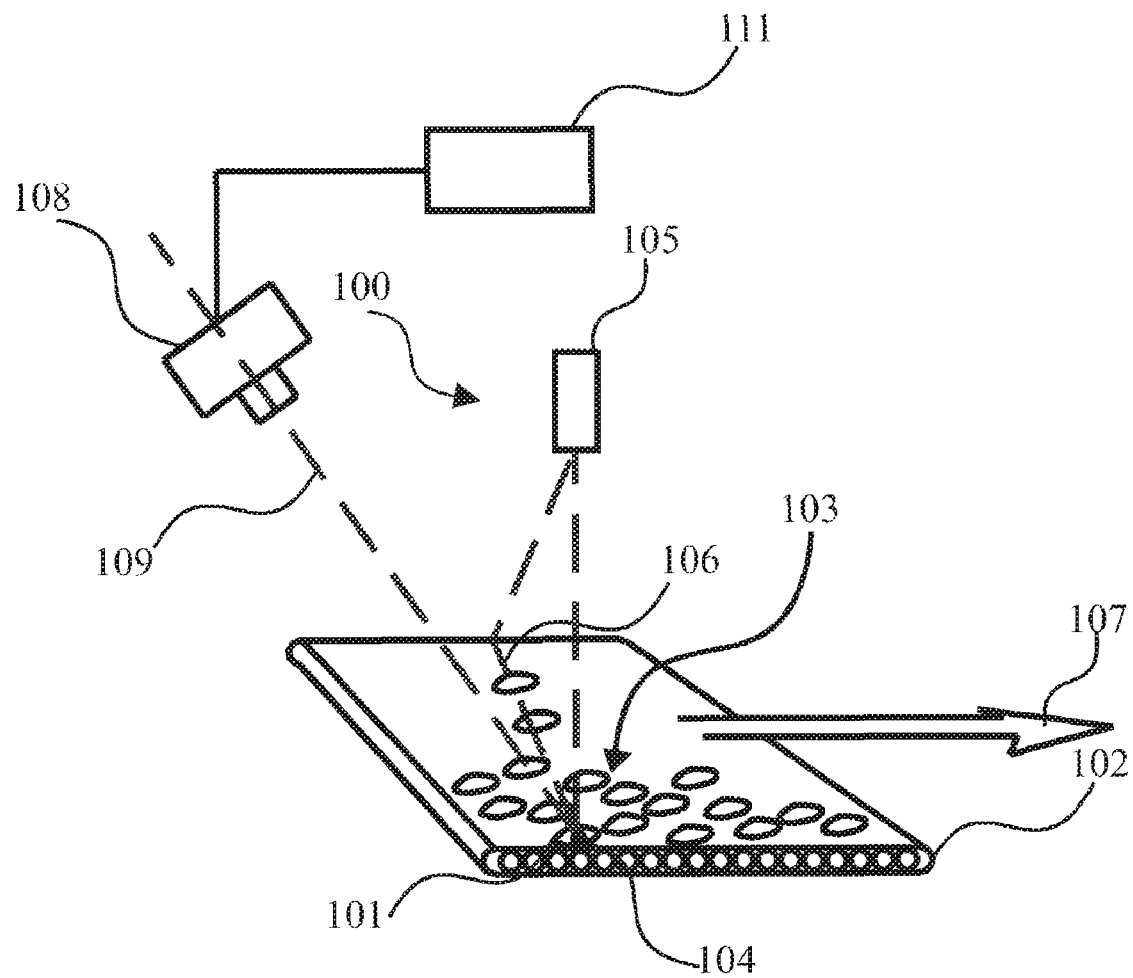
FIG. 1 shows an arrangement for optical analysis in a device according to one embodiment of the invention.

FIG. 1 shows an arrangement for optical measuring 3D surface properties of individual grains 101 for use in a device according to a first embodiment of the present invention and is designated in its entirety by reference numeral 100. The arrangement 100 may be employed in a device for optical measuring on any type of cereal or like crop such as wheat, barley, or other corns, lupins, beans, pulses, Soya beans, coffee and rice.

The device comprises a feeder 102, such as a conveyor belt, arranged to feed a grain sample 103, comprising at least one grain 101, to a place 104 for optical measurement. The feeder 102 may be configured to feed the grains 101 in an arranged manner. Preferably, the grains 101 are fed in parallel rows with a small interval between so that adjacent grains 101 may easily be separated in the optical measurement process. The feeder 102 may be arranged in connection with a hopper (not shown) that places the individual grains 101 in a desired manner on the feeder 102. The direction of movement of the feeder 102 is indicated by the arrow 107. This direction of movement 107 is thus also the direction of transportation of the grains 101 past the place for optical measurement 104.

The arrangement further comprises a light source 105 arranged to illuminate individual grains 101 of the grain sample 103 along a line 106 transverse to the direction of transportation 107 of the grain sample when it passes the place 104 for optical measurement. The light source 105 is preferably a laser that emits light in a plane. The laser light source 105 may be a low power laser requiring minimum safety measures to be taken. The laser light source 105 provides a very well defined line of illumination 106 and gives a distinct reflection that may be recorded and easily converted to a determination of the exact position on a surface of a grain 101 where a reflection occurred.

Figure 2:
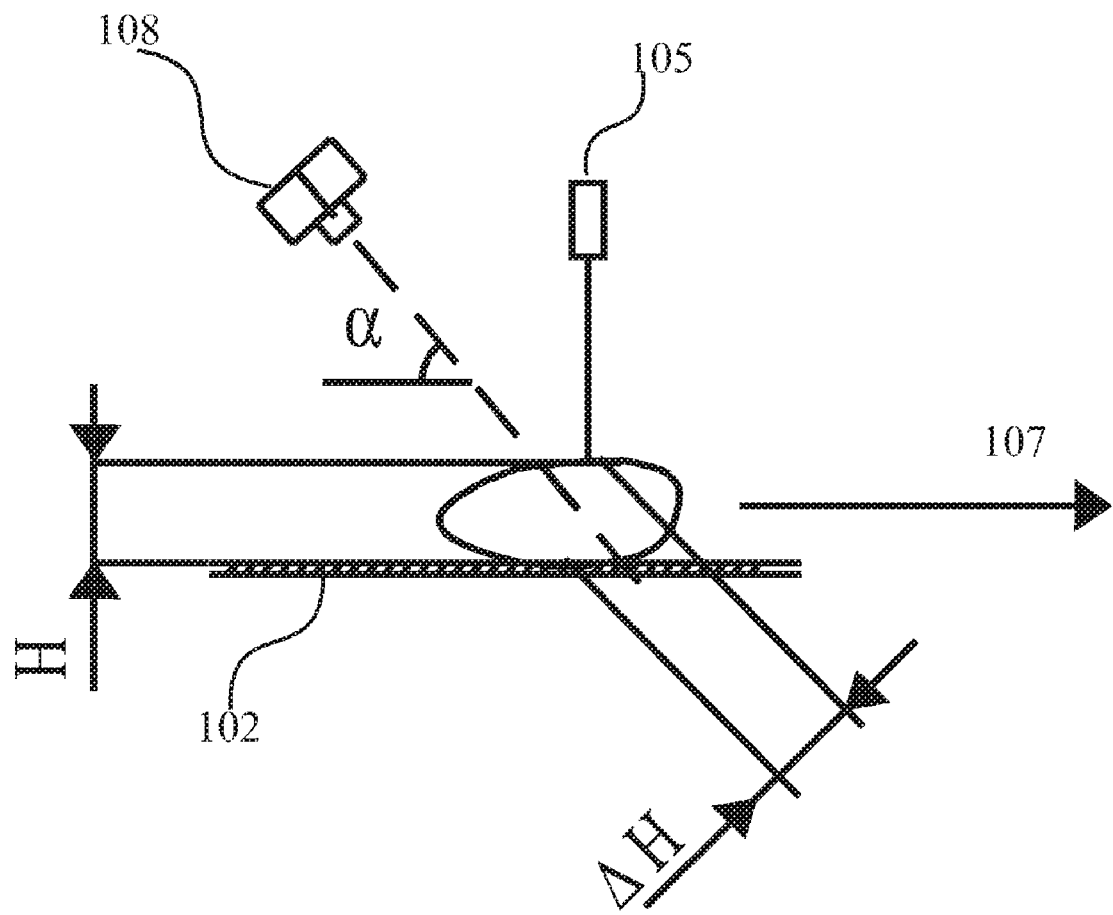
FIG. 2 illustrates determination of a height profile of a grain sample using the arrangement of FIG. 1.

Furthermore, the arrangement 100 comprises a detector 108 arranged to detect the reflection, as indicated by the dashed line 109, from the surface of the individual grains (101) of the grain sample (103) along the illumination line 106. The detector 108 may be an image-acquiring means such as a digital camera. The camera 108 is arranged at an angle α in relation to the feeder 102, as illustrated in FIG. 2. Reflection of the light at different heights, H, over the feeder 102 will thus be imaged in different rows of a camera image.

Figure 3:
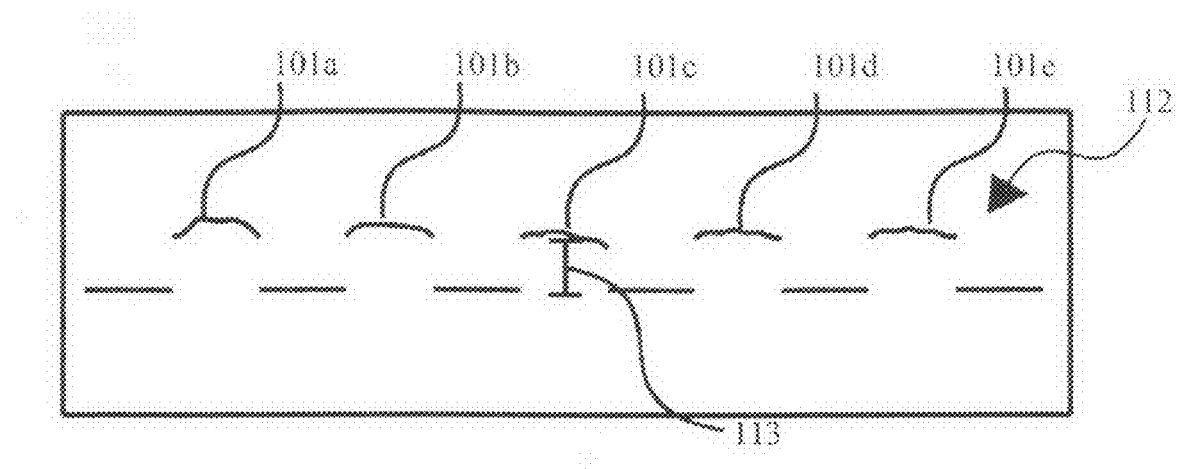
FIG. 3 shows a cross-sectional height profile of a grain sample achieved according to the invention.

An analyzer 111 which is provided and is adapted to process the detected reflection 109 in order to determine a height profile 112 as illustrated in FIG. 3. This height profile 112 is employed in the analyzer 111 as the basis of 3D surface information used in the determination of a quality of the grain sample 103, as will be described in more detail below.

The height H of the grain above a reference plane 102 may thus be calculated according to equation (1) below as:

$$H = \frac{\Delta H}{\cos(\alpha) \cdot res}$$

where H is the actual height of a measured point, ΔH is the pixel distance in the image between a laser point on the feeder 102 (which in use forms a reference plane for measurements) and the measured point and res is the resolution in the image.

An image as detected by the camera 108 is illustrated in FIG. 3. This image may thus be used by the analyzer 111 to calculate the cross-sectional height profile 112 (or surface topography) of one or more an individual grains 101 (here 5, 1a . . . e) of the sample 103 using equation (1) above. Height profiles 112 may be calculated for a plurality of different cross-sections of each individual grain 101a, say, as the individual grains 101 are transported past the place for optical measurement 104. The height profile 112 of FIG. 3 illustrates contours of a plurality of grains 101a . . . d being slightly separated. The straight lines interspacing the curved lines indicate the reference plane, such as the feeder 102 for the grains. The distance 113 between the reflected light from a point on a surface of an individual grain 101 and the reference plane (here the feeder 102) constitutes the term ΔH to be introduced in equation (1).

Figure 4:
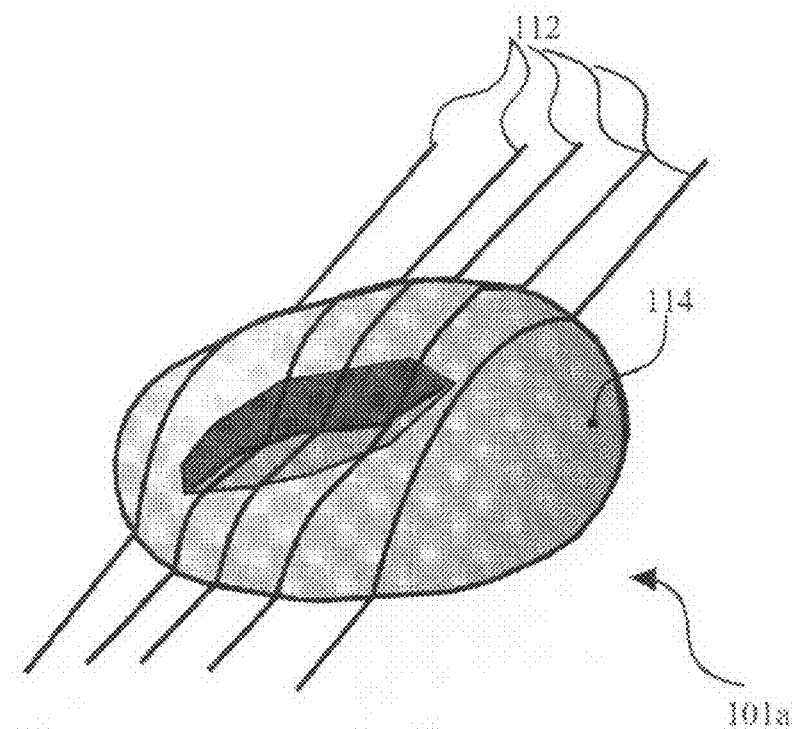
FIG. 4 shows a 3D view of a grain sample according to the invention.

The analyzer 111 is further arranged, in the present embodiment, to generate a 3D surface image 114, as shown in FIG. 4, of each of the one or more grains 101a, say, based on the respective plurality of determined height profiles 112 being obtained as the respective grain 101a is fed past the place 104 for optical measurement and successive images are acquired by the camera 108. As can be seen features in the surface topology can be readily identified and, as will be discussed later with reference to FIGS. 8-9, renders defects in the grain clearly discernable. Alternatively or additionally this so generated 3D surface information of an individual grain 101a may be stored in the analyzer 111 as positional coordinates in a 3D space (for example as Cartesian or polar co-ordinates).

The analyzer 111 then determines a quality of the at least one grain based on the generated 3D surface information. The analyzer 111 may also be arranged to calculate the volume of each grain 101 in a manner known in the art such as disclosed in the publication U.S. Pat. No. 6,369,401. This volume may be used for sorting the grains by size. The volume may also be used for obtaining a relative volume of specific grades of the grains, wherein in the present embodiment the grades are determined using the 3D surface information (topographic information) mapped on to or otherwise collocated with a 2D image of the same individual grains 101. The relative volume may thus give a measure of the volume of a specific grade in relation to the total volume of the grain sample 103. The analyzer 111 may further be arranged to identify foreign objects, such as gravel or dirt, which have shapes that differ substantially from the normal shape and visual appearance of the cereal grains. This identification may be achieved for example by processing a 2D image of the sample using known image recognition techniques. Alternatively the 3D height information may be employed in this regard. The heights of foreign objects tend to be significantly greater than or less than the heights of grains 101. By arranging for the analyzer 111 to perform a height discrimination, based on for example an averaged maximum height derived from a plurality of height profiles 112 from different portions of a same object, then the location of grains can determined and only corresponding portions of the 2D image need be analysed to determine quality.

Figure 5:
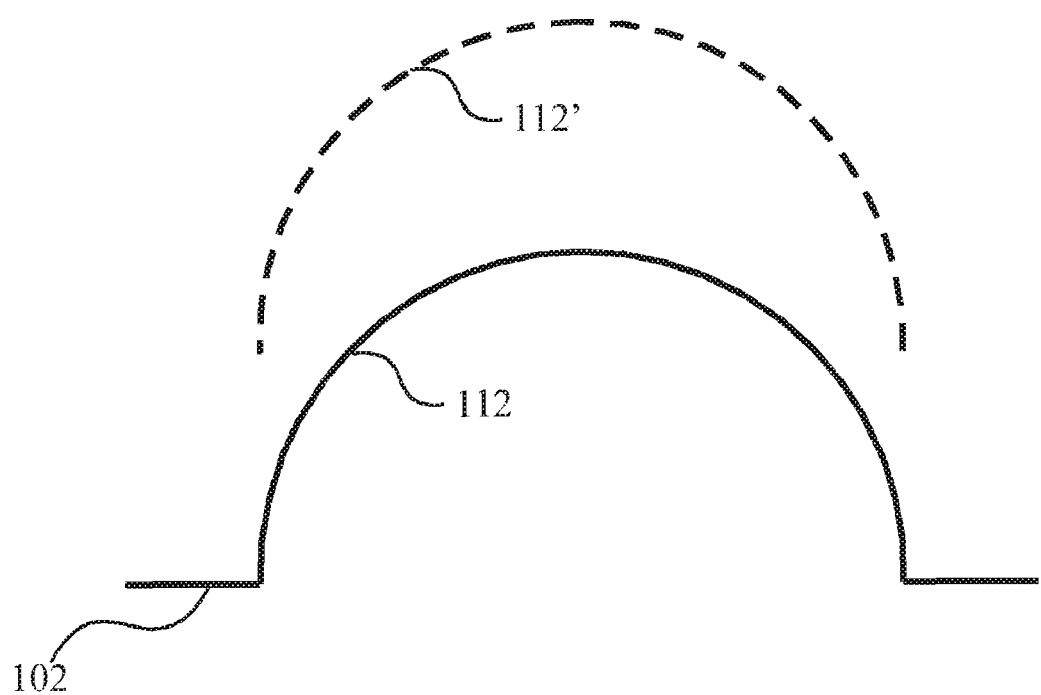
FIG. 5 illustrates the difference of a cross-sectional height profile of a halved grain and a whole grain.

The analyzer 111 may also be arranged to identify defects in the individual grains 101, such as cracked, split, broken or cleaved grains. These defects may be identified using, for example, the 3D surface image 114 or equally the 3D height information alone or in combination with the 2D visual information of an individual grain comparing this to a "normal" or desired 3D surface information of the grain. For example, halved grains, which may otherwise be hard to detect, may now easily be identified using the determined 3D surface image 114, as illustrated in FIG. 5. The halved grains often position themselves with the broken part abutting the feeder 102. Use of a 2D image alone would not be able to detect that the grain is halved and as the image would be of an unaffected part of the grain. However, as shown in FIG. 5, the 3D surface information presents a height profile 112 that is significantly lower than the height profile of an unbroken grain. The detected height profile 112 is shown in FIG. 5 in solid line, whereas the height profile 112' of an unbroken grain is shown in dashed line. Thus, the 3D surface information, as represented by the height profile 112, may be used to easily detect the halved grain. Such halved grains may frequently occur when analyzing Soya beans or peas.

Further, the analyzer 111 may be arranged to detect certain weather damages to the grains. For example, the 3D surface image 114 may be used to identify frost damages, where the grain is thinner and the surface is rougher. Also using the topographical information, the analyzer 111 may be arranged to identify skin remainders on skinned grains. Moreover, the same information may be used to detect sprouted grains having abnormal shapes. Further, some mould and fungal diseases may be identified by the analyzer 111, since grains having such defects have a rougher surface and may show discolouration as compared to normal grains.

The analyzer 111 may comprise one or more units for performing the tasks of determining height profiles, 3D surfaces and 3D images (that is the combined 3D and 2D information for example) and the quality.

Figure 6:
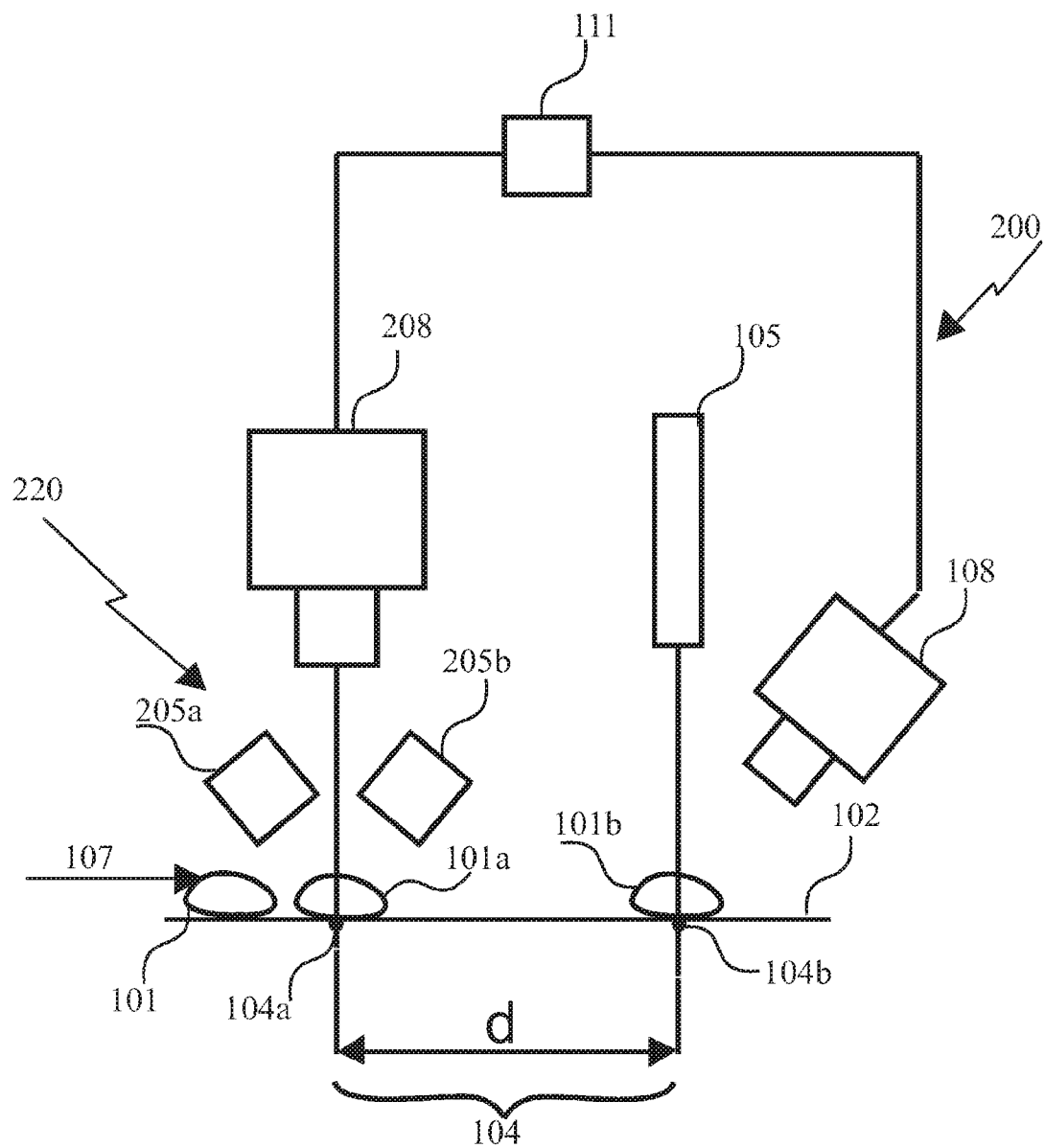
FIG. 6 is a schematic view of a device according to the present invention, incorporating the arrangement of FIG. 1 and FIG. 2 for obtaining combined three-dimensional and two-dimensional information of a sample.

Referring now to FIG. 6, a device 200 according to the present invention is shown which operates to combine 2D image and 3D surface information for analysis of grains from cereals and like crops. The device 200 comprises a feeder 102, as illustrated in FIG. 1. The feeder 102 is arranged to feed a grain sample 103, comprising at least one grain 101, to a first location 104a for optical measurement and further to a second location 104b for optical measurement. These locations 104a and 104b together constitute the place 104 for optical measurement. The set-up at the first location 104a for optical measurement is configured for obtaining 2D plan images of one or more individual grains 101 of the grain sample 103, here illustrated with reference to the individual grain 101a. The set-up at the second location 104b for optical measurement is configured for obtaining 3D surface information of one or more of the individual grains 101 of the grain sample 103, here illustrated with reference to the individual grain 101b, as described above with reference to FIGS. 1-4. The device 200, at the second location 104b for optical measurement, thus comprises a laser light source 105 and a detector 108 arranged at an angle, α, in relation to the feeder 102, in order to determine individual height profiles 112 of grains 101b passing the second location 104b for optical measurement. The first and second locations 104a, 104b for optical measurement are spaced apart with a known distance d, whereby measurements on a same individual grain (101b say) from the different set-ups may easily be combined knowing the speed of transport of the grain sample 103 between the set-ups. The feeder 102 may alternatively be arranged to feed the grain sample 103 in opposite order to the places 204b, 204a for optical measurement.

The device 200 of the present embodiment includes at the first location 104a for optical measurement an arrangement 220 used in the generation of a 2D image of a grain 101. This arrangement 220 comprises light source 205 for illuminating one or more individual grains of the grain sample 103, here illustrated by the grain 101a. The light source 205 may be an incandescent lamp, a light emitting diode (LED) or any other kind of irradiation source that illuminates the grain sample 103 to improve imaging conditions. The light source 205 preferably comprises two units 205a and 205b for illuminating one or more individual grains 101 of the grain sample 103 from different angles simultaneously, whereby a uniform illumination of the individual grains 101a, say, of the grain sample 103 may be achieved. The device 200, at the first location 104a for optical measurement, further comprises a camera 208 that images a 2D plan view of grains 101a of the grain sample 103. The camera 208 may be a line-camera enabling scanning of the grain sample 103 using a continuous speed on the feeder 102. Alternatively, the camera 208 may be any kind of digital camera capable of obtaining a 2D image of the individual grains 101a of the particle sample 103. It should be noted that a plurality of visually separable individual grains may be recorded in a single 2D image.

The image information from each of the first and second set-ups is combined in the analyzer 111 in order to determine a quality of the grain sample 103. Thus, the information from both measurements is used for improving the analysis.

The 2D image may typically be used to classify the grains 101 into different grades based on colour and shape of the grains 101 as viewed in the 2D image. The 3D surface information may then be used as a supplement for identifying certain defects or abnormal shapes of the grains 101 in order to thus improve the analysis performed by the 2D imaging.

Figure 7:
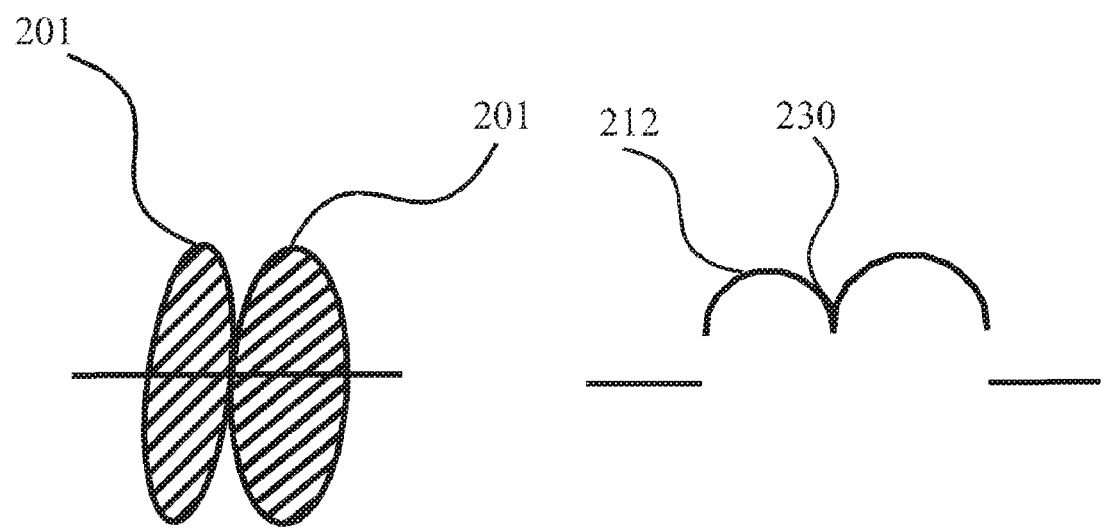
FIGS. 7-9 illustrate sample data that are particularly suitable to be analyzed using the arrangement of FIG. 6.
Figures 8A, 8B:
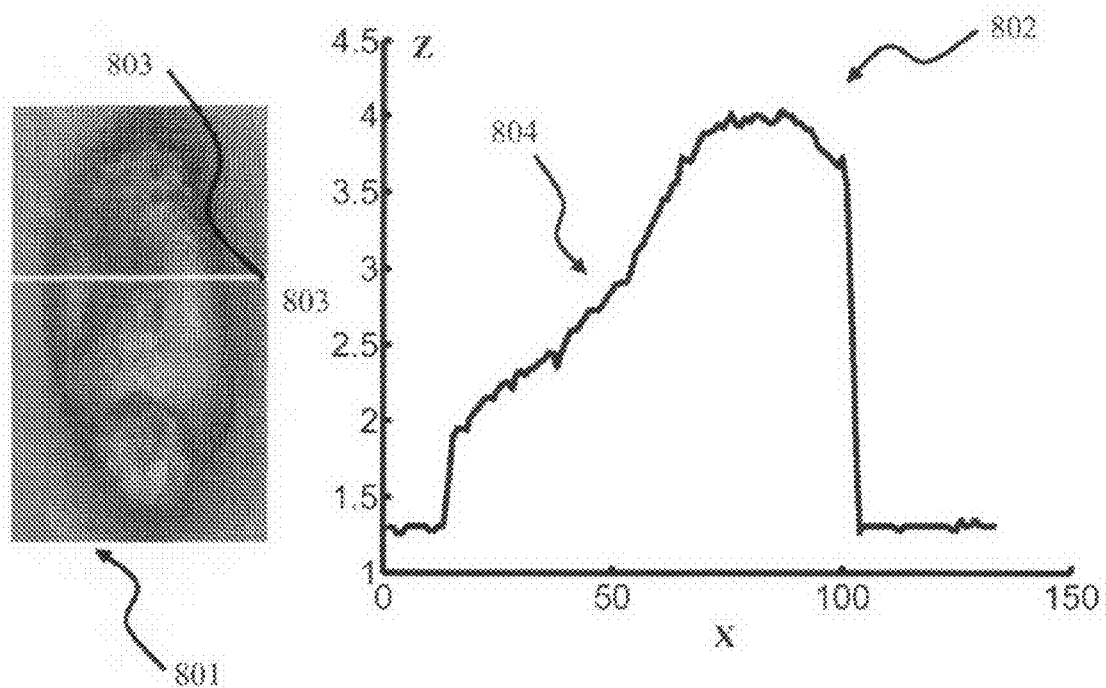
Figures 8C, 8D:
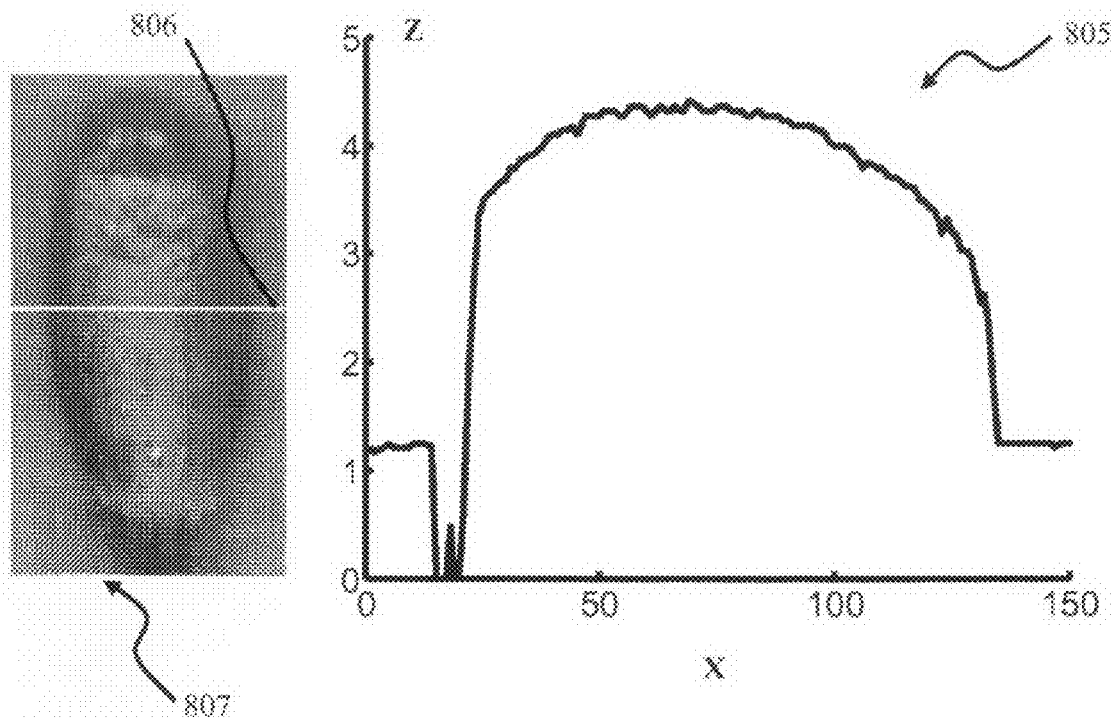
Figures 8E, 8F:
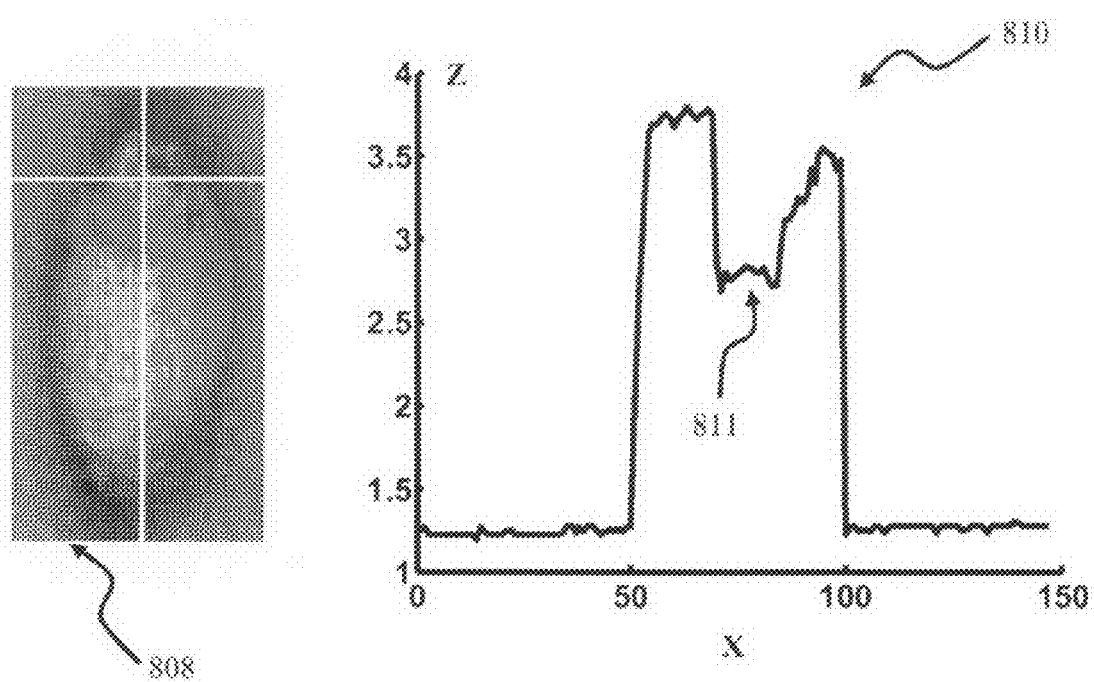
Figures 8G, 8H:
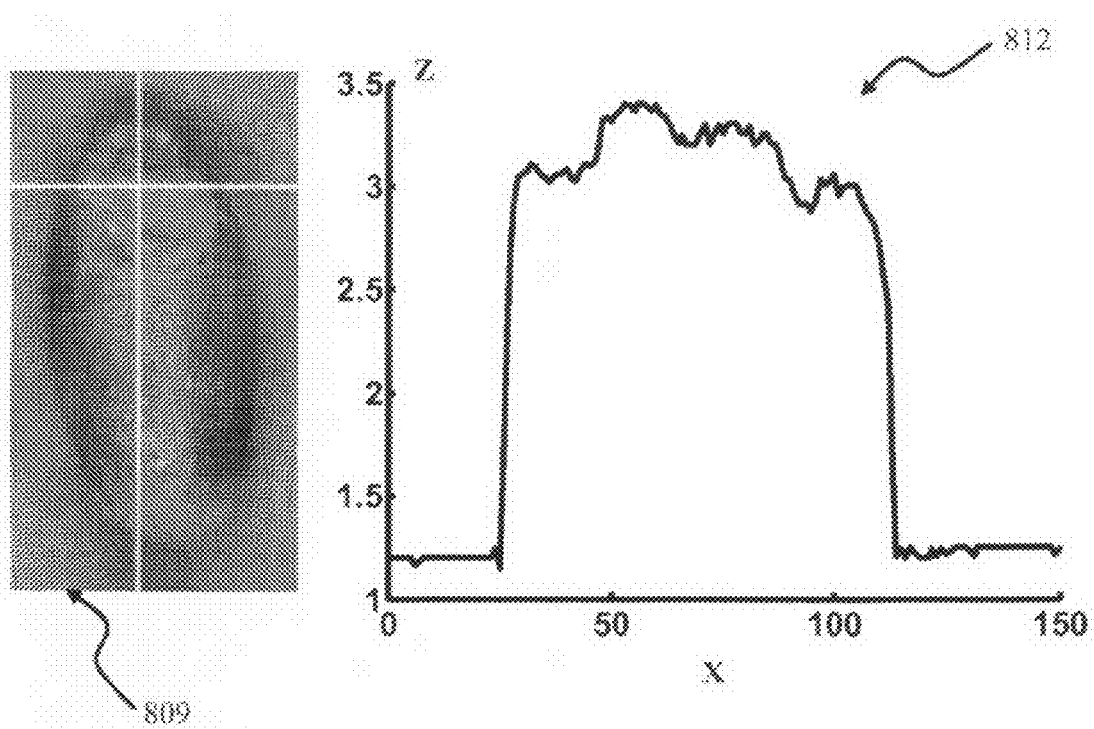
Figures 9A, 9B:
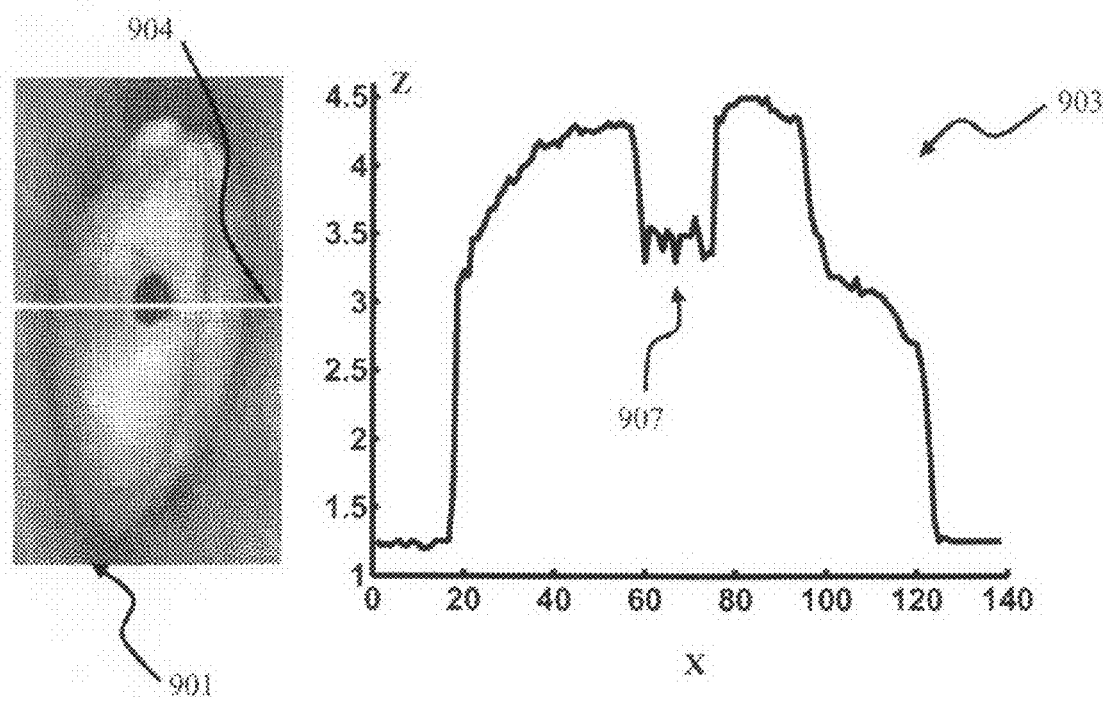
Figures 9C, 9D:
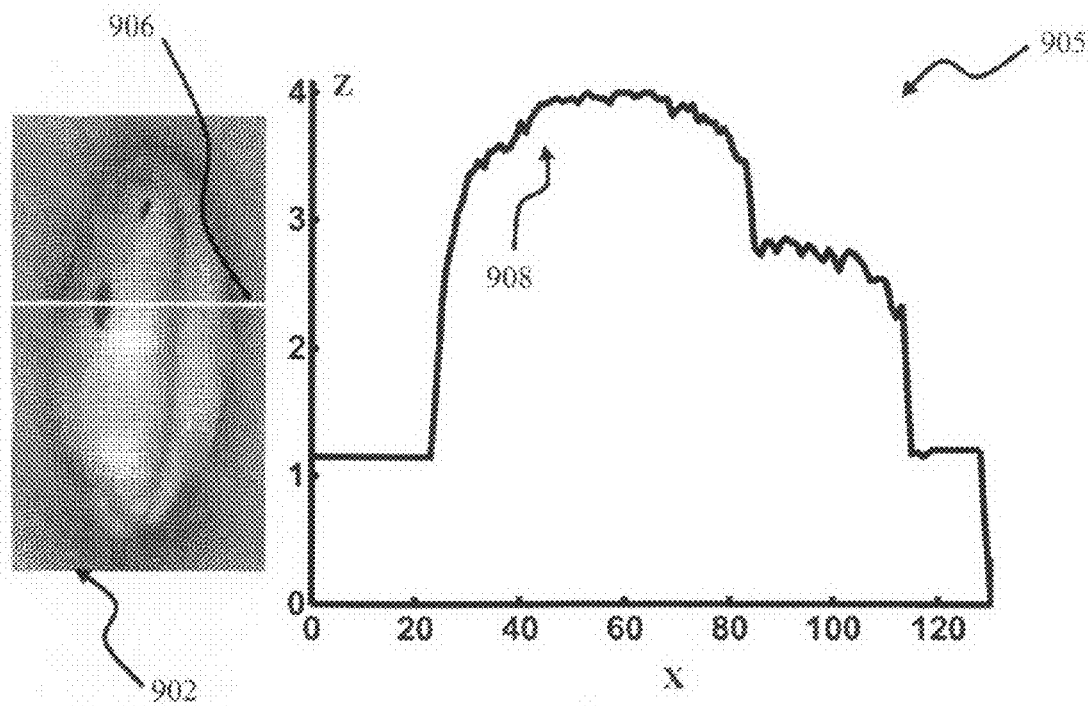

Referring now to FIGS. 7-9, situations where the measurements may be advantageously combined for improving analysis will be described. In FIG. 7a, two grains 201 are shown lying in contact with each other, as viewed in a 2D image. Using this 2D image to separate the grains 201 may be difficult. However, when combining the 2D image with 3D surface information, separating of the grains 201 may easily be achieved. As illustrated in FIG. 7b, the 3D surface information will show an indentation 230 in the height profile 212, which indicates that the height profile 212 is derived from two grains 201. Thus, the 3D surface information may be used to confirm that the 2D image should be segmented into two parts representing two grains 201.

Referring to FIGS. 8 and 9, actual data obtained using a device similar to that of FIG. 6 is shown in order to illustrate how the 3D information may be used to detect irregularities in an individual grain that may be hard to detect in the 2D image. In these Figs the scales associated with the 3D surface information are, for the Z axis in millimetres and for the X axis (in the direction of the line in the 2D image) in pixel number of the image. In FIG. 8a a 2D image 801 of a distorted grain is shown. The distortion is difficult to detect in this image 801. However using the 3D height profile 802 obtained along the line 803 depicted in FIG. 8a sloping surface 804 can be detected. This 3D height profile 802 differs significantly from that obtained from a normal grain as provided in the height profile 805 of FIG. 8d. This profile 805 is obtained along the line 806 depicted in FIG. 8c which is a 2D image 807 of a normal grain. It should be noted that the distortion 804 can be clearly seen from a comparison of the 3D surface information contained in FIG. 8b and FIG. 8d whereas the 2D images of FIG. 8a and FIG. 8c are very similar.

In FIG. 8e a 2D image 808 of a sprouted grain is shown. The sprout is hard to detect in the 2D image as compared with a 2D image 809 of a normal grain shown in FIG. 8g. However, using the 3D height profile 810, an irregular indentation 811 in the surface contour of the grain may be detected. This clearly differs from the height profile 812 of a normal grain illustrated in FIG. 8h. Thus, using the 3D surface information the sprouted grain imaged 808 in FIG. 8e may be detected and correctly classified.

Considering now FIG. 9. In FIG. 9a, a 2D image 901 of an insect damaged grain is shown. A comparison with a 2D image 902 of a grain having a surface discolouration clearly illustrates that a comparison of 2D images 901 and 902 would make classification of a grain as being damaged due to insect damage extremely difficult. However, a comparison of the 3D surface profile 903, obtained along the line 904, with that 905 of a normal grain, obtained along the line 906 makes identification easier. An indentation 907 is detectable in the profile 903 associated with the black spot in the image 901 of the insect damaged grain whereas none is visible in the region 908 of the profile 905 associated with the image 902 of the discoloured grain. However a comparison of the 3D height profile 810 associated with the image 808 of the sprouted grain with that profile 903 associated with the insect damage grain would both reveal the presence of indentations 811 and 907 respectively. A comparison of the respective 2D images 808 and 901 would clearly differentiate between sprouted and insect damaged grains. The 2D images may also be employed to determine whether or not the object being imaged is in fact a grain or a foreign body. Thus, an analysis based on both 2D image and the 3D surface information may be used to improve the detection and classification of such surface defects and result in a more reliable quality classification being made by the analyzer 111.

Figure 10:
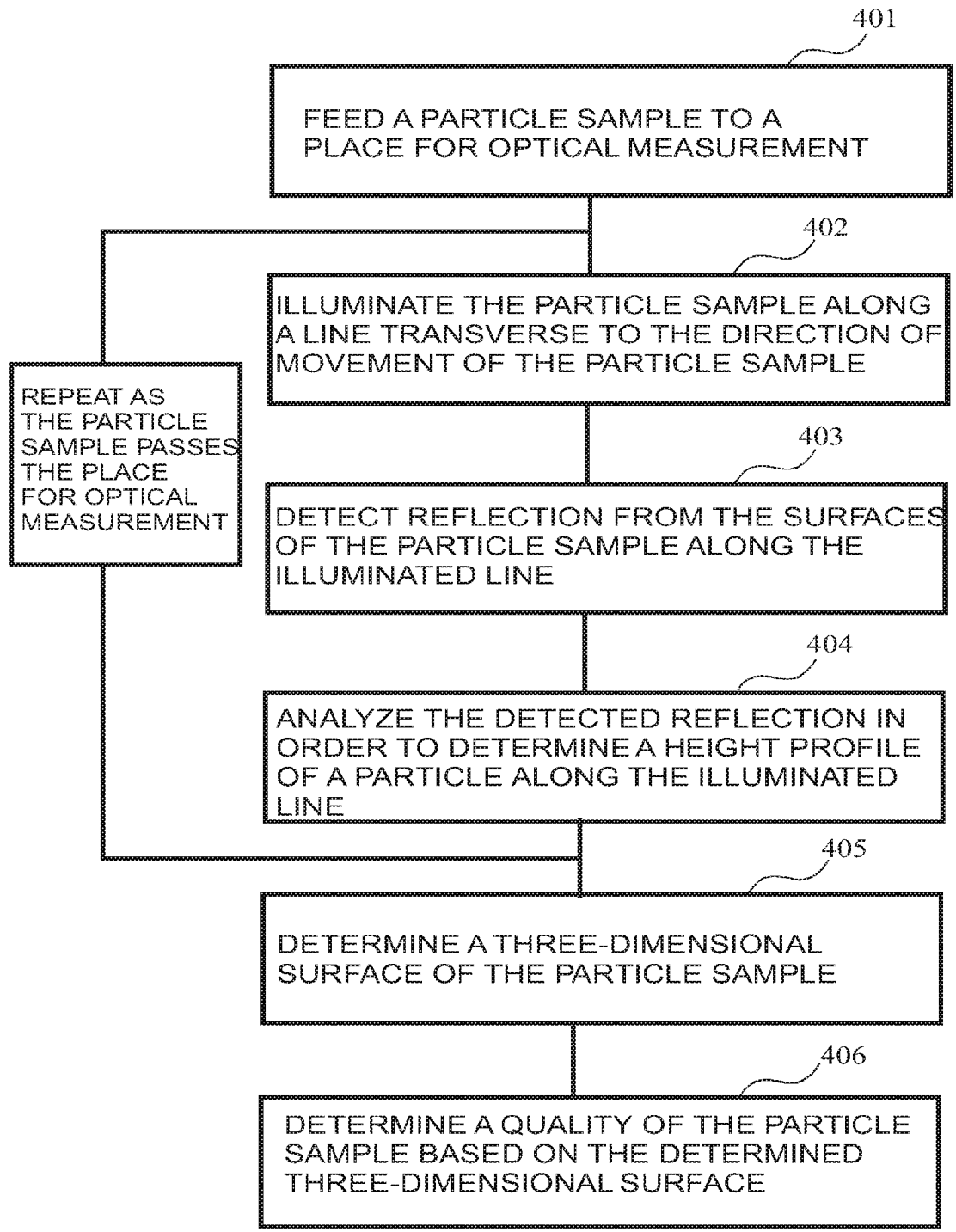
FIG. 10 shows a schematic diagram of the steps in a method for use in an exemplary device according to the invention.

Referring now to FIG. 10, a method for optical determination of a quality of a grain sample will be described. A grain sample is provided to the feeder of the device for optical measurement. The feeder feeds, step 401, the grain sample to a place for optical measurement where a light source illuminates, step 402, the grain sample along a line transverse to the direction of movement of the grain sample when the particle sample passes the place for optical measurement. A detector detects, step 403, reflection from the surfaces of the grain sample along the illuminated line and an analyzer analyzes, step 404, the detected reflection in order to determine a height profile of at lease one grain along the illuminated line. The steps of illuminating 402, detecting 403 and analyzing 404 are repeated as the grain passes the place for optical measurement in order to determine, step 405, a 3D height profile (surface contour map) of the entire grain that is based on or consists of a plurality of height profiles along the illuminated line of different portions of the grain.

The analyzer then determines, step 406, a quality of the particle sample based on the determined 3D surface information in the form of the height profile of the entire grain.

From a user's perspective, the process of measurement can be described according to the following. A user of the device inserts a grain sample into a hopper in connection with the device for optical measurement. The user inputs required sample information and selects the quality factors that are to be measured. The analysis is initiated and when the device has carried out the steps previously mentioned the results are displayed to the user and/or stored in a memory. Subsequently the sample is removed, either manually with a sample collection cup or automatically by the device.

Figure 11:
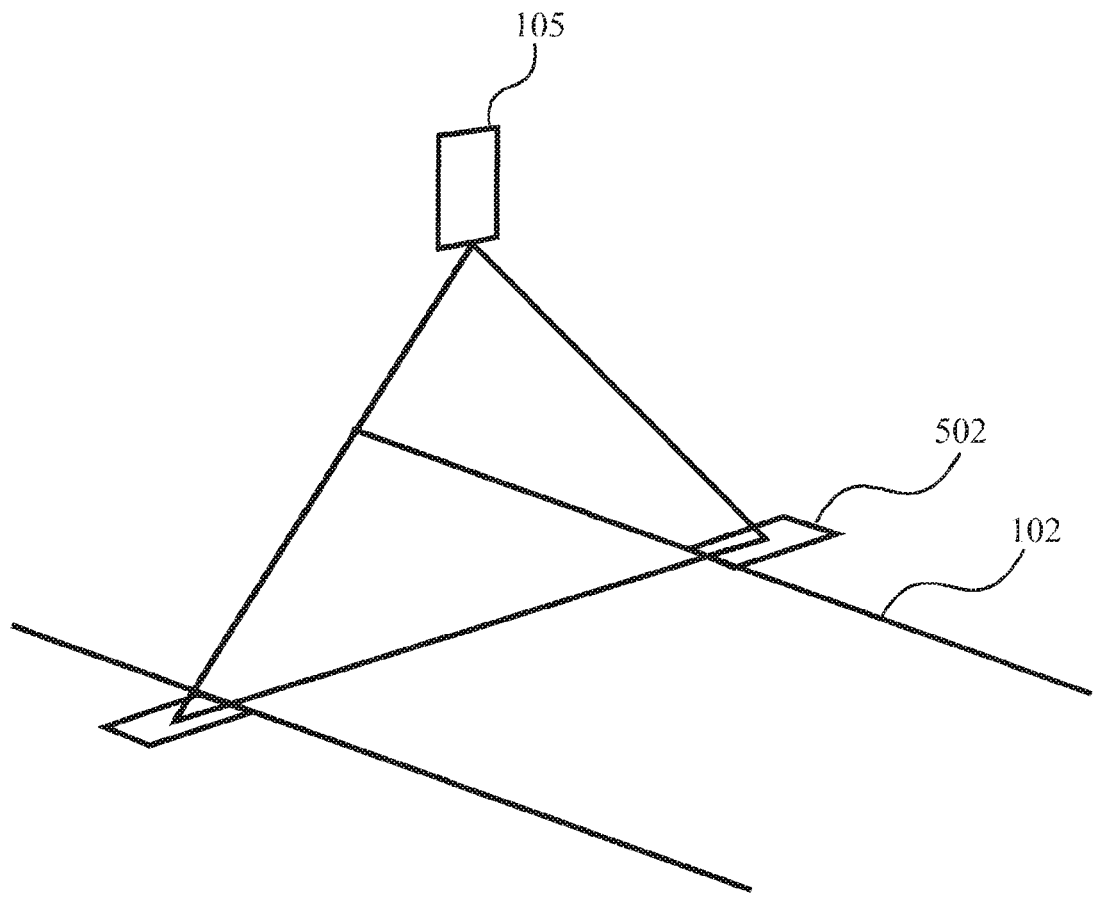
FIG. 11 shows a calibration set-up in a device according to one embodiment of the invention.

Calibration of the device is advantageously carried out by arranging reference plates 502 on the sides of the feeder 102 where the projected beam of light crosses the feeder 102 transversely, as illustrated in FIG. 11. When the plane of the feeder 102 is in alignment with the reference plates 502, the height profile 112 as determined by the detector 108 and analyzer 111 will constitute a straight line, providing a simple and precise process for alignment.

It should be emphasized that the preferred embodiments described herein are in no way limiting and that many alternative embodiments are possible within the scope of protection defined by the appended claims. For example, a second camera may be arranged to view the illuminated line. The second camera may be arranged at a position opposite to the light source from the first camera. Thus, the first and second camera together will be able to view the entire height profile of the grains. Using only one camera, some parts of a grain may be obscured. Thus, using two cameras a more accurate 3D surface image may be obtained.

Also, according to another alternative, the 3D surface information of a grain may be obtained by means of two or more digital cameras being arranged to view the grain from different angles, while the entire grain is illuminated. Images of the grain obtained by the two or more digital cameras may then be used in order to determine a 3D shape.

The invention claimed is:

1. A device for optical analysis of a quality of grains from crops, comprising:
   a feeder, which is arranged to feed a grain sample, which comprises at least one grain, to a place for optical measurement,
   an optical system, which is adapted to illuminate individual grains of the grain sample at the place for optical measurement and to detect illumination after its interaction with a surface of the individual illuminated grain, and
   an analyzer, which is adapted to receive the detected illumination and to process the same to determine a quality of said grain sample, wherein the analyzer is adapted to process the detected illumination to generate three-dimensional surface information of an individual grain of the grain sample and to analyse the three-dimensional surface information to determine the quality.

2. The device as described in claim 1 wherein the optical system comprises components relatively disposed to illuminate and detect illumination for processing to generate two-dimensional image information for the same individual grain; and in that the analyzer is adapted to analyse the three-dimensional surface information together with the two-dimensional image information of the same individual grain to determine the quality.

3. The device as described in claim 2 wherein the analyzer is adapted to perform a comparison of the two-dimensional image information and the three dimensional surface information from a same physical region of a surface of the same individual grain to determine the quality.

4. The device as described in claim 2 wherein the analyzer is adapted to process the three-dimensional surface information and the two-dimensional image information of the same individual grain by mapping said three-dimensional surface information on to said two-dimensional image to generate a combined relief image for analysis to determine the quality.

5. The device as described in claim 1 wherein the optical system comprises
   a laser light source, which is arranged to illuminate the grain sample along a line transverse to a direction of movement of the grain sample; and
   detection means including a detector, which is arranged to detect illumination reflected from the surface of an individual grain of the grain sample along the line; and in that the analyzer is adapted to analyze the detected reflected illumination to determine a height profile of the individual grain of the grain sample along said line and to generate the three-dimensional surface information based on a plurality of so determined height profiles of the individual grain as that grain is transported in the direction of movement through the line.

6. The device as described in claim 1 wherein the analyzer is adapted to determine a height profile as the three-dimensional surface information by comparing distances between the surface of the individual grain with a plane.

7. A method for optical analysis of a quality of grains from crops, comprising the steps of
   feeding a grain sample, which comprises at least one grain, to a place for optical measurement,
   illuminating said grain sample at said place for optical measurement,
   detecting illumination after its interaction with said grain sample,
   analyzing said detected illumination to determine a quality of said grain sample, characterised in that said step of analyzing comprises processing the detected illumination to generate three-dimensional surface information of individual grains of the grain sample, and
   determining a quality of said grain sample from an analysis of said three-dimensional surface information.

8. The method as described in claim 7, wherein the step of processing the detected illumination also generates two-dimensional image information of the same individual grain; and in that the step of determining a quality of said grain sample comprises an analysis of the three-dimensional surface information in combination with the two-dimensional image information.

* * * * *